(12) United States Patent
Roman Espinoza et al.

(10) Patent No.: US 8,470,569 B2
(45) Date of Patent: Jun. 25, 2013

(54) HYDROMETALLURGICAL PROCEDURE FOR THE PRODUCTION OF FERRIC-SULFATE FROM FAYALITE SLAG

(75) Inventors: Enrique Anselmo Roman Espinoza, La Florida (CL); Héctor Dario Jordan Gutierrez, Quilicura (CL); Leandro Mauricio Padilla Iglesias, Providencia (CL); Pedro Antonio Morales Cerda, La Reina (CL); Ricardo Badilla Ohlbaum, La Reina (CL)

(73) Assignee: Biosigma S.A., Colina (CL)

( * ) Notice: Subject to any disclaimer, the term of this patent is extended or adjusted under 35 U.S.C. 154(b) by 205 days.

(21) Appl. No.: 12/958,972

(22) Filed: Dec. 2, 2010

(65) Prior Publication Data

US 2011/0136198 A1    Jun. 9, 2011

(30) Foreign Application Priority Data

Dec. 3, 2009    (CL) .................................. 2156-2009

(51) Int. Cl.
*C12P 3/00*       (2006.01)
(52) U.S. Cl.
USPC ................ 435/168; 435/41; 75/316; 75/425; 210/726; 210/601; 210/748.18; 210/758
(58) Field of Classification Search
None
See application file for complete search history.

(56) References Cited

U.S. PATENT DOCUMENTS

| 3,206,303 | A | * | 9/1965 | Goren | 423/339 |
| 5,158,686 | A | * | 10/1992 | Kigel | 210/713 |
| 7,387,770 | B2 | | 6/2008 | Wilkinson et al. | |
| 2007/0048213 | A1 | | 3/2007 | Wilkinson et al. | |

FOREIGN PATENT DOCUMENTS

| CL | 45508 | 12/1909 |
| CL | 0935 2007 | 3/2007 |

OTHER PUBLICATIONS

Anand, S et al. "Leaching behaviour of copper converter slag in sulphuric acid", Transactions of The Indian Institute of Metals, 1980, 33(1): 70-73.*
Mazuelos, A et al. "Ferric iron production in packed bed bioreactors: influence of pH, temperature, particle size, bacterial support material and type of air distributor", Minerals Engineering, 2001, 14: 507-514.*
Büchner, et al. "*Industrial Inorganic Chemistry*." VCH, Publisher (1989) pp. 525-526.
Decreto Supremo 148. (2004) pp. 8-9.—Translation provided.
Fan et al. "A process for synthesizing polymeric ferric sulphate using sulphur dioxide from coal combustion." *Int. J. Environmental Tech. & Mgmt.*, vol. 2, No. 4 (2002) pp. 393-401.
Ingledew, W. John "*Thiobacillus ferrooxidans*—The Bioenergetics of an Acidophilic Chemolithotroph." *Biochimica et Biophysica Acta*, vol. 683 (1982) pp. 89-117.
Li et al. "The Preparation of Inorganic Coagulant-Poly Ferric Sulfate." *J. Chem. Tech. Biotechnol.*, vol. 68 (1997) pp. 219-221.

\* cited by examiner

*Primary Examiner* — Jon P Weber
*Assistant Examiner* — Chunyuan Luo
(74) *Attorney, Agent, or Firm* — Merchant & Gould P.C.

(57) ABSTRACT

The present invention corresponds to a commercial production process of ferric sulfate whose plant can be installed scaled to the requirements of the process of application of the bio-produced ferric solution based on fayalite slag generated in copper smelting plants. No previous process has established as its method of industrial application the use of these smelter slags in the bio-production of ferric sulfate solutions at concentrations above 20 g/L, including a stage of acid-slag leaching in dynamic heaps with control of generated silica and subsequent precipitation of colloidal silica and other impurities in a stirred reactor in the invented process. The ferrous solution free of colloidal silica and other impurities is subjected to a process of bio-oxidization of the clean ferrous solution by microorganisms adapted to these metallurgical solutions.

10 Claims, 4 Drawing Sheets

HYDROMETALLURGICAL PROCEDURE FOR THE PRODUCTION OF FERRIC-SULFATE FROM FAYALITE SLAG

This application claims benefit of Serial No. 2156-2009, filed 3 Dec. 2009 in Chile and which application is incorporated herein by reference. To the extent appropriate, a claim of priority is made to the above disclosed application.

FIELD OF THE INVENTION

This application discloses an industrial procedure for the production of aqueous solutions of ferric sulfate with concentration levels of ferric ions above 20 g/L. The raw material of this new process corresponds to fayalite slag corresponding mainly to fayalite species ($FeSiO_3$) that have has high iron (40-50%) and silicon (10-15%) contents, and are generated in Copper Smelting Plants being currently disposed in dumps as industrial waste from the pyrometallurgical copper production process.

The proposed process is characterized by being undertaken in three successive stages: (1) Obtainment of ferrous sulfate solutions during leaching of fayalite slag with sulfuric acid solutions (2) Precipitation of silica and removal of impurities from the ferrous sulfate solution, and (3) Bio-oxidation of the clean ferrous sulfate solution.

This new procedure allows provision in continuous operation of a ferric solution for use in various applications in which ferric input is essential, for example: (1) The treatment of industrial metallurgical effluents containing high levels of arsenic and heavy metals, which requires as main provision, ferric ions to precipitate and environmentally stabilize arsenic as ferric arsenate, and heavy metals stably adsorbed in a matrix of ferric oxide; (2) The ferric acid leaching of ores or of sulfide basic metals concentrates that require a stage of release of these metals in acid solution, and in oxidation conditions of high electrochemical potential, and (3) The water treatments processes that require ferric sulfate as a flocculating reagent that captures toxic impurities present in the water to be purified.

Thus obtaining ferric solutions by applying the invention disclosed in this application represents a technological alternative of easy and economical deployment in industrial plants.

The invention disclosed here corresponds to a hydrometallurgical procedure for the production of ferric sulfate solutions with ferric iron concentrations greater than 20 g/L, considering as raw material, a low-cost iron resource that is present in the fayalite slag generated in copper smelting plants and which are sent to dumps. The new procedure is characterized by being carried out in three successive stages and operated continuously: (1) Leaching of granulated and classified fayalite slag (100% particle diameter larger than 0.1 cm) in dynamic-heap or fixed-bed modalities, using discarded industrial acid solutions and sulfuric acid; (2) Precipitation of silica and other impurities from the ferrous-sulfate-rich solutions generated in the leaching of the slag, which contain various impurities such as silica, aluminum, arsenic, and antimony among others. At this stage these impure solutions are treated by a thermal procedure corresponding to a specific coagulation and precipitation of colloidal silica so as to obtain a potentially commercial byproduct of silica gel, $SiO_2 \cdot 2H_2O$, and a low-silica content ferrous leach solution of less than 400 ppm. Alternatively, the ferrous leach solution is neutralized with lime slurry, operating with flow and pH control at the output of the neutralization reactors, the design criteria being the specific consumption of lime (CaO) per unit of volume of ferrous acid solution to be neutralized and the concentrations of impurities that need to be precipitated. This stage of the procedure produces a ferrous solution with silicon content of less than 400 ppm and low concentration levels of other impurities, as well as environmentally sound waste—mainly gypsum and ferric hydroxide; (3) bio-oxidization stage: clean and neutralized ferrous solutions are prepared with sulfuric acid at a pH within the range of 1.4 to 1.8, before being sent to a bioreactor operating continuously with a productivity above 4.2 kg. $Ferric \cdot hr^{-1} \cdot m^{-3}$, generating ferric sulfate solutions that contain a concentration in Fe (III) ions greater than 20 g/L.

BACKGROUND INFORMATION OF THE INVENTION

The ferric sulfate, used mainly in water treatment and stabilization of industrial effluents, is obtained commercially, usually in its solid state (approximately 80-60% of soluble ferric ion), or in aqueous solutions containing ferric ion up to 240 g/L. Commercial production processes vary depending on the availability of raw materials and their economic acceptability. The method that accounts for the highest production of the reagent worldwide is based on the oxidization of ferrous sulfate solutions, the main byproduct of the titanium and aluminum industry. The ferrous sulfate solutions are oxidized by hydrogen peroxide, with ferric sulfate later crystallized by evaporation from these ferric solutions (W. Büchner, R. Schiliebs, G. Winter and KB Büchel "Industrial Inorganic Chemistry", VCH, Publisher, 1989, pages 525-526). A second industrial method is based on the oxidization and dissolution of magnetite, $Fe_3O_4$ (Chilean Patent No. 45508, 2009). In this method, the magnetite is attacked under pressure in glazed autoclaves with concentrated sulfuric acid, followed by oxidization of the ferrous ion content in the acid solution with hydrogen peroxide—this given that 24.1% of the iron present in magnetite is in ferrous iron form. A similar patent (U.S. Patent Application U.S. 20070048213) considers iron oxides as raw material, which is treated with sulfuric acid in an autoclave at high temperature and pressure. Other patents and publications describing the obtainment of polymeric ferric sulfate in aqueous solution consider ferric oxides and ferrous sulfate as raw materials (U.S. Pat. No. 7,387,770), using oxygen or nitrogen oxides as oxidizing agents (Fengting Li et al, Journal of Chemical Technology & Biotechnology, Vol. 68, (2) pp 219-221 (1997)), or sulfur dioxide and ferrous sulfate (Maohong Fan et al, International Journal of Environmental Technology and Management, Vol 2 (4), pp 393-401, (2002)). Moreover, various steel processing industries and galvanic industries employ an acid discard solution called "pickling" from which it is possible to obtain ferrous sulfate heptahydrate as a byproduct on a large scale, which, dissolved in water, is then oxidized with hydrogen peroxide in an acid environment. Another method, applied since ancient times and on a smaller scale for commercial production of commercial ferric sulfate, is the dissolution of metallic iron contained in iron scrap, which is treated with sulfuric acid, obtaining gaseous hydrogen and ferrous sulfate solution as a result; this ferrous solution is generally oxidized with hydrogen peroxide.

As noted above, the invention disclosed in this document is based on the oxidization of ferrous sulfate solutions obtained during the leaching of fayalite slag. The ferrous solutions obtained during this process also have significant concentrations of silicon (in the range of 1 to 15 g/L), as well as aluminum and arsenic, among other impurities in the slag, which are simultaneously and partially released during the process. In addition to the aforementioned impurities there are those in the leach solution fed to the process, for example when employing industrial acid effluents.

Silica ($SiO_2$) contained in the ferrous acid solutions used in slag leaching, is presented in the form of a colloid composed of microscopic and sub-micron particles, which have, in general, meta-stable behavior at pH below 2.4. Physicochemical studies on destabilization of colloidal solutions of silica, and their subsequent precipitation, are based on the electrostatic decompression of the electrically charged colloid surface caused by the addition of trivalent ions such as $Al^{3+}$ and $Fe^{3+}$, or also of divalent ions such as $Mg^{2+}$ and $Zn^{2+}$ in a defined pH range. The coagulation of colloidal silica can be increased by the addition of coagulating agents and commercial flocculants. In the industry, the coagulation of silica from moderately acidic aqueous solutions by the addition of specific chemical agents such as $Al^{3+}$, $Mg^{2+}$ ions, silica or "activated sand", followed by flocculation, obtains a residual sludge with over 60% p/p solid content. In the absence of flocculating agents, the content of solids in the final pulp does not exceed 10% p/p.

The last stage of the process disclosed in this document is the catalyzed oxidization by microorganisms in a bioreactor of the clean ferrous sulfate solutions obtained during the fayalite-slag leaching and subsequent precipitation of silica and impurities. The bio-oxidization of ferrous solutions is known chiefly in the field of natural and induced bioleaching of sulfide ores, which generates mine water and acid leaching solutions respectively. This natural phenomenon occurs by the action of iron(II)-oxidizing microorganisms, which obtain the energy required by their metabolic processes from the oxidization of ferrous to ferric ions in the aqueous medium, (W J Ingledew. 1982. *Thiobacillus ferrooxidans*: The Bioenergetics of an acidophilic chemolithotroph. Biochimica et Biophysica Acta 683: 89-117.), according to the following chemical reaction:

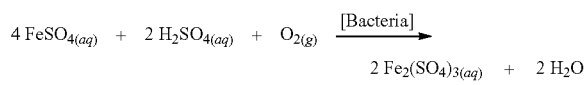

Such organisms may include the following species: *Acidithiobacillus ferrooxidans, Leptospirillum ferrooxidans* and *Leptospirillum ferriphilum*. The Chilean Patent Application 935-2007 of Apr. 3, 2007, discloses a ferric solution production process that uses as raw material: magnetite, ores or ore concentrates which are partially dissolved in sulfuric acid, releasing the ferrous ion. The ferrous solution is bio-oxidized by the *Leptospirillum ferrooxidans* bacteria cultures in a bioreactor stirred at 30° C., containing magnetite slurry.

The invention presented in this application differs from the procedures mentioned above in that: i) the fayalite slag used as raw material is industrial waste without economic value, unlike magnetite, which is a high-priced commercial product; ii) during the purification of the ferrous solution obtained in the slag leaching stage, a commercial byproduct such as silica gel, is generated and iii) bio-oxidization of the purified ferrous solution is carried out in a bio-oxidization bioreactor, with immobilized biomass, of the "air-lift" type, that operates continuously with short residence times (5 hours for the bio-oxidization of solutions containing 25 g/L of ferrous ion), which represents an operational and economic advantage.

The present invention corresponds to a commercial ferric sulfate production process whose plant can be installed scaled to the requirements demanded by the application of the bio-produced ferric solution process, using fayalite slag generated in copper-smelting plants. No previous process has established as a method of industrial application the use of this smelter slag in the bio-production of ferric sulfate solutions with ferric iron concentrations greater than 20 g/L including in the invented process a stage of acid slag leaching in dynamic heaps with control over the resulting silica and subsequent precipitation of colloidal silica and other impurities in a stirred reactor. The ferrous solution, free of colloidal silica and other impurities, is subjected to a process of bio-oxidization of the clean ferrous solution by microorganisms adapted to these metallurgical solutions.

DETAILED DESCRIPTION OF THE INVENTION

The source of iron in the invention disclosed in this document is the fayalite slag from an electric furnace for reductive slag cleaning, produced by copper smelting plants, which contains mainly iron and silicon (40-50% iron and 10 to 15% silicon, on average). This waste material from pyrometallurgical processes has a high chemical reactivity in sulfuric acid, generating ferrous sulfate according to the following chemical reactions:

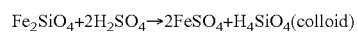

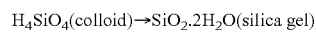

In addition to releasing iron (II) the acid leaching of slag, with aqueous solutions of sulfuric acid, or alternatively with acid solutions available in metallurgical plants, such as the raffinate solutions from copper solvent-extraction plants, or other available acidic solutions (e.g. refinery waste solutions and sulfuric acid plant effluents and smelter dust plant acid leaching effluents), also releases impurities such as silicon in the state of colloidal silica ($SiO_2$), aluminum, arsenic and metallic values (copper, molybdenum, zinc) in low and variable concentrations depending on the input to the slag leaching. The general block diagram of the process described in this invention is shown in FIG. 1, illustrating each stage of the process described in this invention.

Figure 1:
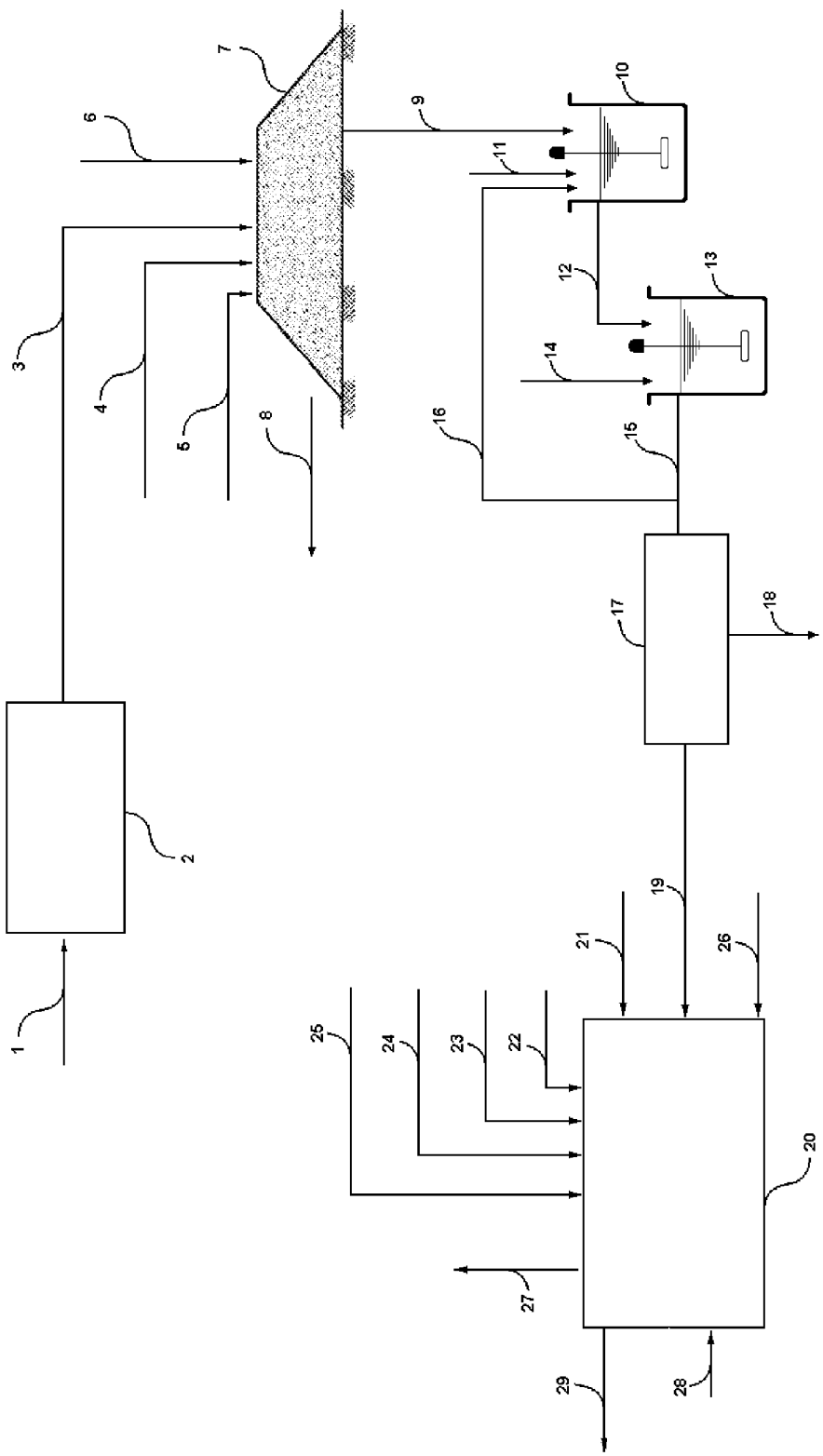
FIG. 1 shows a flow chart illustrating the ferric sulfate production procedure through acid leaching of granulated classified fayalite slag, operated in dynamic heap or fixed-bed mode, which also includes the stages of precipitation of silica and other impurities from solutions produced in the leaching of slag and followed by a final stage of bio-oxidization of the clean ferrous solutions produced during the previous stage.

The following describes each of the stages referred to in FIG. 1.

(1) Drying, sorting and disposal of granulated slag in fixed-bed heaps or modules: Granulated slag (a) produced in slag cleaning electric furnaces in copper smelting plants is transported with the humidity typical of the granulating process to the storage area near the slag heap leaching area. It is then arranged in a pad of a defined size for solar drying till residual moisture of less than 1% is achieved, with the residence time of this material in the pad depending on the slag layer thickness and natural heating conditions of the location of these solar pads. This granulated slag (1) is alternately dried in a rotary kiln with external heating, at a temperature within the range of 100-200° C. for a residence time according to the design of the drying oven. The dry slag—with moisture contents below 1%—is sent to be classified in a vibrating screen in order to separate fine slag whose particles are smaller than 0.1 cm. This fine material (2) is returned to the slag dumps, whereas the bulk material (3), granulated to particle sizes larger than 1 cm, is transported and disposed of in heaps ranging in size from 0.70 m to 3 m high, with a standard slope angle and a crown with an irrigated surface fitted to the required flow of solution. This granulated classified slag can be alternatively arranged in fixed-bed leaching modules or gabions sized according to the ferrous sulfate and ferric iron solution production needs.

(2) Acid leaching of slag: this unitary operation is carried out in dynamic fixed-bed heaps or modules or gabions (7). In the first case, as an example, granulated classified fayalite slag (3) is arranged in 0.7 m to 3 m high dynamic heaps (7). Achieving satisfactory drainage of the slag heaps, with irrigation rates that can operate between 20-100 $L \cdot hr^{-1} \cdot m^{-2}$ with no flooding problems and with hydraulic stability for this type of heap, requires a granulated-slag particle-size greater than 1 mm diameter, according to the slag-granulating procedure making it possible to reach a size of 0.5 cm diameter. These dynamic heaps are irrigated with solutions from hydrometallurgical plants (4), with the addition of sulfuric acid (5) whose concentrations are in the range of 15 to 70 g/L, with a controlled and modulated irrigation rate sufficient to allow the obtainment of a percolated liquid (9) with the maximum concentration of ferrous ions, while minimizing the concentration of silica in solution. In general, to achieve a minimum concentration of silica in solution, irrigation rates range from 15 to 60 $L \cdot hr^{-1} \cdot m^{-2}$, so that in this case the value of 1-4 g/L of silicon in the pond for the final reception of the ferrous sulfate-rich solution, is not exceeded. The number of slag heaps and the operation time for each of them is determined by the leaching kinetics curve and the daily production of ferrous sulfate required to bio-oxidize this ferrous solution and for its subsequent applications. In this operational mode of leaching slag in heaps, for both fresh and depleted heap situations, and with proper management of intermediate solutions, the final concentration of colloidal silica in the percolating solution reaches a maximum average concentration, as silicon, of less than 4 g/L. This relatively low value of silicon content in the ferrous solution is explained by the $Al^{3+}$ ion content and other ions such as $Fe^{3+}$, $Mg^{2+}$, $Zn^{2+}$, which are released from the slag itself and cause coagulation and precipitation of silica within the leach heap. The ferrous sulfate solution (9) is stored in the final pond and is then pumped to the first silica precipitation reactor (10). The depleted heaps, (8), washed with water (6) and drained, are sent to waste dumps as an environmentally sound solid waste in accordance with leachability and reactivity standard tests (EPA leachability tests; Supreme Decree 148 of the Republic of Chile, 2004, p. 8-9).

(3) Silica precipitation: This stage can be carried out according to two processing alternatives:

(A) Selective thermal precipitation of colloidal silica: This operation is described in FIG. 2. The slag leaching ferrous solution (1) with high colloidal-silica content, exceeding 2 g/L as Si content, and with a pH value around 2, is transferred to a stirred reactor (2) which is heated by a heater (3). This system operates in continuous mode at a temperature of 80-90° C., with stirring and residence time of 30-60 minutes. The colloidal silica, $SiO_2 \cdot nH_2O$, in this reactor is subjected to a thermal process of coagulation and precipitation as $SiO_2 \cdot 2H_2O$ silica gel. Under these thermal conditions and owing to the presence of trivalent ions such as $Al^{3+}$ and $Fe^{3+}$, in addition to $Mg^{2+}$, $Zn^{2+}$ ions present in the acidic slag leaching solution, a destabilization of the colloidal silica is induced by compression of the electrical layer of colloidal particles, thus coagulating the colloidal silica. Due to the above, these trivalent ions of aluminum and iron (III) as well as the divalent ions of magnesium and zinc, furnished by the same fayalite slag during acid leaching, play the role of coagulating agents. The slurry (4) leaving the silica precipitation reactor is transferred to a cooling and resting pond, and from this pond, the cold pulp is sent to a filter press or a continuous band, or to be centrifuged (5) to be separated as a stable precipitate (6) that is user-friendly in terms of separation, washing and subsequent transporting. In a subsequent refining process the final product—a technical-grade silica gel, $SiO_2 \cdot 2H_2O$—is obtained. The operating conditions in the colloidal silica thermal precipitation reactor are: (a) The reactor (2) for thermal coagulation and precipitation of silica operates continuously at a temperature in the range of 80-95° C.; (b) Residence time: 30-60 minutes; (c) Stirring: 80 to 200 rpm. (D) Cooling of the resulting slurry at a temperature below 15° C. during a rest period of at least 15 hours. The obtained cake is washed with water in the same separator equipment (5) and then treated by drying, re-pulping of the solid, washing and finally subjected to drying in a fluidized bed dryer or sun drying pad where the soaking water is removed, while the network water of the solid is incorporated into a final compound as crystallization water. The dry solid-silica gel-formulated as $SiO_2 \cdot 2H_2O$, can be marketed for multiple industrial uses. Thus, the filtered or centrifuged (7) ferrous solution acquires minimum contents of silicon (less than 100 ppm) and other impurities, ensuring the subsequent bio-oxidization stage of the solution. This stage of colloidal silica precipitation, achieved by thermal coagulation and subsequent cooling of the slurry followed by separation of the silica, has a silicon precipitation efficiency greater than 95%, ensuring a ferrous solution with silicon content in the range of 70-400 ppm and ferrous ion content exceeding 20 g/L.

Figure 3:
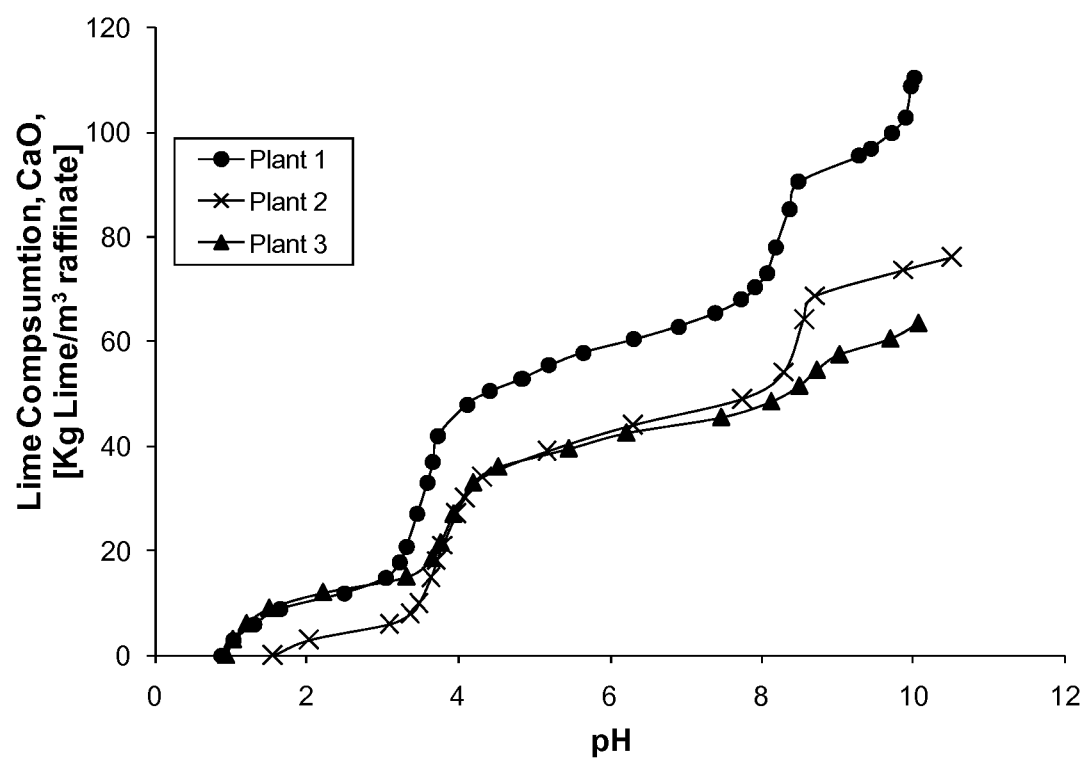
FIG. 3 shows the curves of lime consumption per unit volume of the ferrous solution raffinate to be neutralized and comes from the previous slag leaching stage, and is applied to raffinate solutions generated in three industrial hydrometallurgical plants. Also shown is the pH at which total precipitation of this impurity is obtained.

(B) Precipitation of silica at room temperature with lime slurry: This stage refers to FIG. 1. This second alternative of abating the silica present in the ferrous solution produced by the acid slag leaching corresponds to its precipitation, in addition to other impurities contained in the leaching solution, through the addition of lime slurry at 10% p/v. This operation is carried out in continuous mode according to the following description: The ferrous solution generated in the previous acid slag leaching stage (9) is transferred to two stirred reactors (10) and (13) arranged in series, which in turn continuously receive a stream of lime slurry (11) and (14) respectively, maintaining an appropriate pH to allow efficient precipitation of silica, aluminum, and other impurities. The precipitation pH and the use of lime in operation mode depend on the contents of other impurities (mainly $Al^{3+}$) that come with the silica in the solution. If the slag heap feed solution is composed only of water and sulfuric acid, the operation value (set point) of the pH in the second precipitation reactor has a value in the range of pH 3 to 4; whereas, for a slag heap feed solution composed of a raffinate solution from solvent-based copper extraction plants plus sulfuric acid, the precipitation pH in the second reactor is adjusted in the range of 3.8 to 4.3, a value which depends mainly on the concentrations of $Al^{3+}$ and $Fe^{3+}$ contained in the raffinate solution, this is determined by the experimental curve of lime consumption that is specific of the solution subjected to the treatment as shown in the neutralization curves in FIG. 3. This figure shows an example of the specific consumption of lime (CaO) for the precipitation of several metals in the raffinates of three hydrometallurgical industrial Solvent-Electrowinning Leaching-Extraction plants. The residence time for silica precipitation in each reactor is one hour, and the operation is carried out at room temperature. The outgoing slurry from the second reactor (15) finally contains the precipitate of silica, $SiO_2 \cdot nH_2O$, and gypsum, $CaSO_4 \cdot 2H_2O$. The latter contributes to the agglomeration of the precipitated silica, leaving a residue with a higher percentage of solids in the final slurry. This slurry is transferred to a storage and rest pond for 8 to 10 hours to stabilize the precipitated silica, before being transferred to a filter or centrifuge (17) where a solid residue (18) is obtained and sent directly to a landfill as environmentally stable waste, as has been verified by the application of leaching tests and geotechnical tests regulated by existing legislation.

(4) Bio-oxidization of treated ferrous solution: The clean ferrous solution with low concentrations of silicon and other impurities (19) obtained in the previous operation, is conditioned by the addition of specifically formulated nutrients (23) (in order to maintain the metabolic activity of microorganisms used in this continuous bio-reactor) and adjustment of pH between 1.5 and 1.7 with sulfuric acid (21), before being sent to a bio-oxidization reactor of the "airlift" type (20) which operates continuously with a consortium of microorganisms (22) adapted to this environment, where microorganisms of the genus *Leptospirillium* (*L. ferriphilum* and *L. ferrooxidans*) prevail, immobilized in a solid base (24) adjusted with a determined particle size. Other potentially useful microorganisms at this stage of the present invention are *Acidimicrobium ferrooxidans, Acidithiobacillus ferrooxidans, Ferrimicrobium acidiphilum, Acidiphillium* spp, *Ferroplasma acidiphilium, Sulfobacillus* spp., and in general any acidophilic microorganism capable of oxidizing ferrous ion.

This reactor receives a continuous injection of air (26). The air expelled from the bioreactor with less oxygen content is released into the atmosphere (27). Given that the oxidization of iron is accompanied by the consumption of acid equivalents, the process requires a constant supply of sulfuric acid to maintain a stable pH within the reactor (25). The residence time of this reactor is 4-11 hours, depending on the concentration of iron (II) in the feed, and the operating temperature is in the range of 20-40° C. Operating continuously in this bioreactor as described, an average productivity of 4.2 Kg·hr$^{-1}$·m$^{-3}$ ferric ion is achieved, yielding a clear solution of ferric sulfate (29), in $Fe^{3+}$ ion concentrations of over 20 g/L as required by metallurgical plants, water treatment plants and in general any plant that requires this intake through a low-cost process.

According to this description of the bio-hydrometallurgical process disclosed here, the efficiency of acid slag leaching in dynamic heaps is 30 to 90% in iron released in a solution of ferrous sulfate with low colloidal silica content. The cutoff point of operation on the iron leach heap is determined by the kinetic curve of iron release, and by the cost associated with this unitary operation, where a critical factor is the silica precipitated in the heap so that, above 60% efficiency in the release of iron there is a risk of decline in the percolation rate of the heap, leading to a possible major event of flooding of the heap. The efficiency of silicon precipitation, on the other hand, is greater than 95%, and the bio-oxidization of ferrous to ferric is 100%.

Example 1

Described here is a hydrometallurgical operation validated in a pilot plant scaled for the production of 54 Kg/day of ferric sulfate, $Fe_2(SO_4)_3$, equivalent to a plant flow of 25 L/hr of ferric solution obtained in the form of slag leaching in 1.8 m-high leaching columns. This example is based on the results obtained in the pilot plant illustrated in FIG. 1, which highlights the three areas of operations corresponding to this process: (1) Area of granulated and classified slag leaching in leaching columns; (2) Area of precipitation of silica and impurities, and (3) Area of ferrous to ferric bio-oxidization.

(1) Area of granulated classified slag leaching (>1 mm diameter): Two leaching columns, 1.8 m high, and with internal diameter of 0.31 m (7) were loaded with 276 Kg each of granulated classified fayalite slag (3), (0.1 cm.<<0.5 cm diameter). They were then irrigated with industrial plant effluent solution (4) with the addition of acid (5), and whose chemical characterization is shown in Table 1.

TABLE 1

Characterization of the industrial slag irrigation solution

| Fe g/L | Si ppm | Cu g/L | Al g/L | Mo ppm | As g/L | Cl ppm | Sulfate g/L | Nitrate ppm | $H_2SO_4$ g/L |
|---|---|---|---|---|---|---|---|---|---|
| 4.10 | 80 | 0.76 | 0.91 | 1.12 | 0.34 | 260 | 92 | 100 | 73.8 |

Table 2 shows the composition of granulated classified slag used in this example of leaching columns.

TABLE 2

Characterization of granulated classified slag (>1 mm diameter)

| | Element | | | | | |
|---|---|---|---|---|---|---|
| | Fe | Si | Zn | Cu | Mo | As |
| % | 45.20 | 13.20 | 2.54 | 1.15 | 0.22 | 0.18 |

Figure 4:
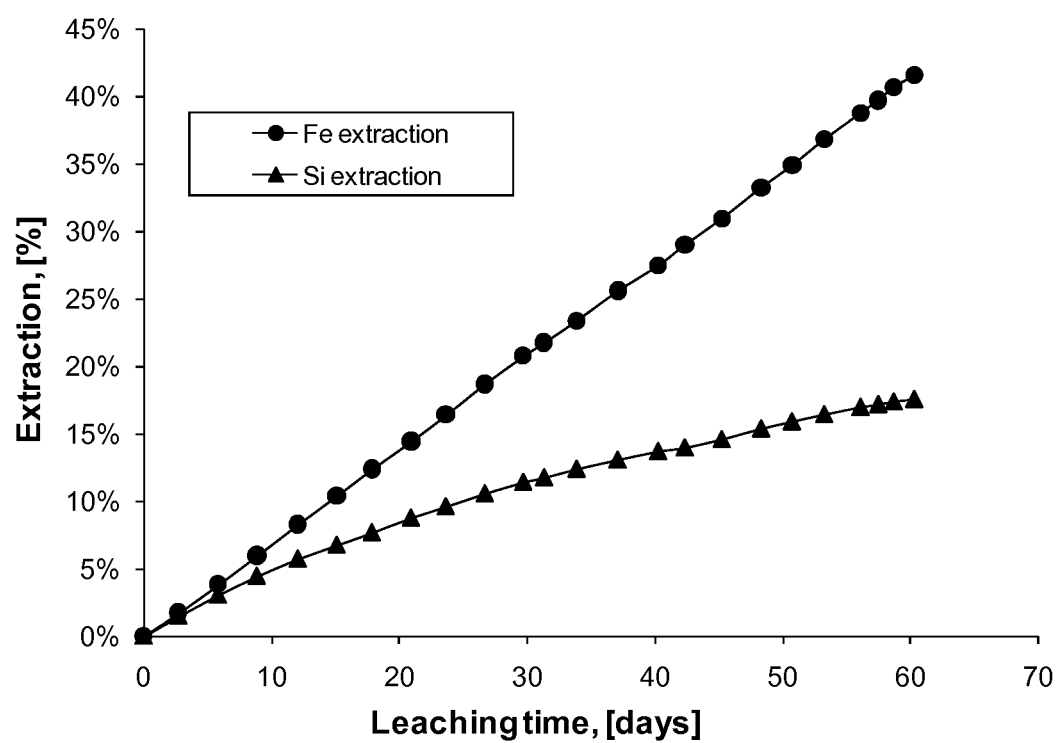
FIG. 4 Recovery of iron and silicon: it represents the kinetic design curve of the leaching of granulated classified fayalite slag in dynamic heaps, at room temperature; irrigation solution of 60 g/L sulfuric acid, irrigation rate of 20 $L \cdot hr^{-1} \cdot m^{-2}$.

Leaching columns were operated at room temperature and at an irrigation rate of 20 L·hr$^{-1}$·m$^{-2}$ during 60 days of irrigation. The behavior of these two leached columns is determined by the kinetic curve of leaching of iron and silicon, as shown in FIG. 4, which is due to an almost linear relationship of iron release over time, showing that this is a behavior controlled by chemical reaction, unlike the chemical silica release behavior, which is affected by the formation of colloids and coagulation of silica gel within the leaching column.

The results of this continuous operation are expressed in terms of the obtainment of 4.5 m$^3$ of a solution rich in ferrous ions (9) whose average and final characterization of the ferrous solution obtained in this example is presented in Table 3.

TABLE 3

Characterization of the ferrous solution obtained from slag leaching.

| Fe g/L | Si g/L | Cu g/L | Al g/L | Mo ppm | As ppm | Cl ppm | Sulfate g/L | Nitrate ppm | $H_2SO_4$ g/L |
|---|---|---|---|---|---|---|---|---|---|
| 28.51 | 4.48 | 1.21 | 2.72 | 60 | 50 | 310 | 88.7 | 190 | 0.71 |

Based on these results, the efficiency of slag acid leaching after 60 days of operation is 42% iron and 18% silicon. An operation over a greater number of days, while achieving greater efficiency in terms of iron in solution, is inconvenient due to the risk of mass precipitation of silica gel, $SiO_2.H_2O$, within the column, stopping the draining of leached solution and so increasing the likelihood of flooding of the column. Because of this, the process design contemplates a safe operation time of up to 60 days under the operational conditions described above.

(2) Area of precipitation of silica and Impurities: A total of 4.5 m³ of slag leaching solution effluent (9) in columns, with a chemical characterization as shown in Table 3, is sent to the area of precipitation of silica and impurities whose flow diagram is illustrated in FIG. 1. The acidic ferrous solution is transferred from the storage tank at a flow of 8.5 L/hr. to two stirred tanks arranged in series (10 and 13), which in turn separately receive a flow of 0.66 L/hr of lime slurry at 10% p/v prepared in a stirred tank. The quality of the lime to be used is defined as a commercial input, ground to a P80 size <200 #ty, <0.075 mm, with low sand or silica content to prevent the pipes transporting pulp to the plant from clogging up. Both acid solution neutralization ponds are automatically controlled in terms of regulating the flow of lime slurry so as to maintain in each reactor a pH value of 3.8 and 4.3 in the slurry going out of each reactor, (10) and (13) respectively. The lime slurry flows needed in order to maintain these pHs are 0.36 L/hr and 0.30 L/hr for the first and second reactor respectively. In addition to the lime slurry feed, the reactor (10) receives recirculation slurry (16) issued from the pond cooling a 10% slurry of the precipitate accumulated in the pond. This is designed to make use of this recirculated slurry that plays a "seed" or "core creation" crystallization role that accelerates the precipitation of impurities and ultimately increases the size of particles in the final precipitate, thereby improving the settling and filtration of the final waste. The slurry leaving the second stirred neutralization tank (13) is transferred to a cooling pond where the precipitate remains from 10 to 20 hours to stabilize the precipitated silica, and is then transferred to a stirred container from which it is transferred to the filtering equipment (17). The filtered solid (18) is subjected to cycles of washing and blowing, obtaining a "cake" with 68% humidity. This high humidity is a component of the solid-soaking water and mainly of the "chemical water", which corresponds to water molecules that are integrated into the molecular structure of precipitated silica gel. This water gives the precipitate a greater volume. To reduce the content of this "chemical water" integrated into the precipitated colloidal silica, the precipitate is dried in a solar drying pad, requiring 2-3 days to obtain a dry residue with 10-20% humidity. The advantage of this is that this residue acquires geotechnical properties suitable for confinement in a landfill. This procedure is equivalent to "hardening" of a material that includes "chemical water" in its solid-state molecular structure. The environmental stability of the obtained waste is ensured by the results of leaching tests and geotechnical tests set by environmental standards.

Example 2

Figure 2:
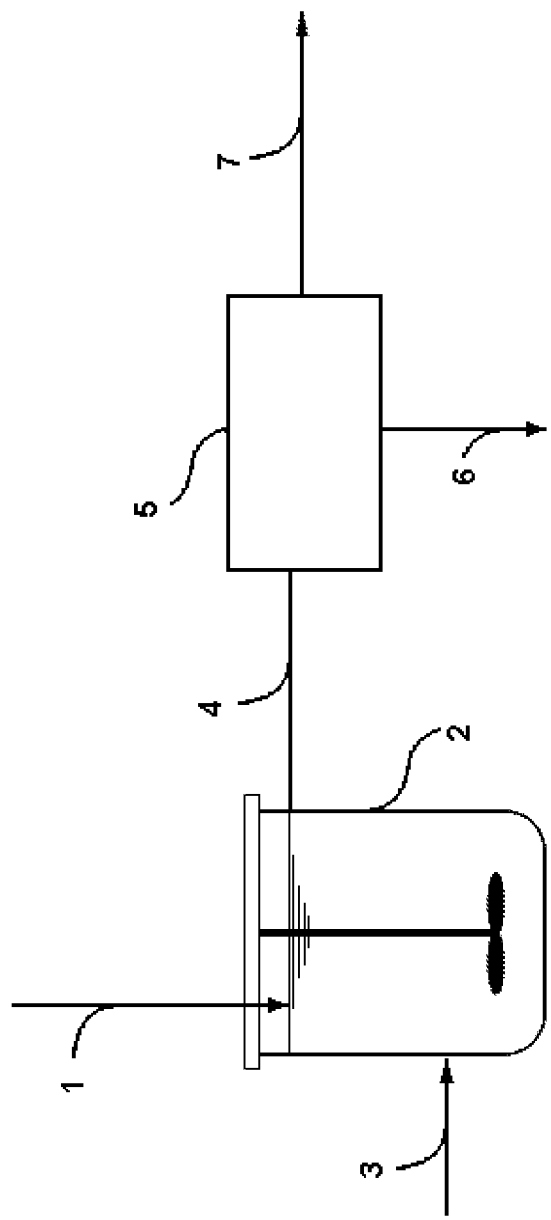
FIG. 2 shows a flow chart representing the specific coagulation and thermal precipitation of colloidal silica, induced by trivalent ions ($Al^{3+}$, $Fe^{3+}$) and divalent ions ($Mg^{2+}$, $Mn^{2+}$, $Zn^{2+}$) present in the heap leaching ferrous solution, thus obtaining a byproduct of silica gel, $SiO_2.2H_2O$.

This example describes the extraction of colloidal silica, $SiO_2.H_2O$, from the ferrous solution generated in the granulated classified slag leaching heap by thermal treatment, obtaining a final product of silica gel, $SiO_2.2H_2O$. FIG. 2 illustrates the equipment used. Thus, a volume of 1.8 m³ of ferrous solution generated by slag leaching is transferred to the reactor (2) which is equipped with a heater, a mechanical stirring system and a water steam condenser to maintain a constant volume of the solution. The ferrous solution (1) with an initial concentration of silicon of 4.5 g/L, whose chemical characterization is presented in Table 3, is subjected to heating at a temperature of 95° C. for 60 minutes, and with agitation at 200 rpm. After 60 minutes, all the silica contained in the reactor undergoes coagulation accelerated by the presence of trivalent ions $Al^{3+}$ and $Fe^{3+}$ as well as other ions such as $Mg^{2+}$ and $Zn^{2+}$ presents in the feeding ferrous solution. The coagulated solution (2) is then transferred to a cooling and rest pond for a period of 10-20 hours. After this time the precipitated solid is filtered in the filter-press (5). The precipitated silica (6) is then re-pulped in a stirred reactor with a volume of water corresponding to half the weight of the humid solid, producing a solid percentage of 66% when considering the wet solid, or 13% when considering the dry solid. The slurry is stirred for 30 minutes and then filtered. This last operation is designed to extract minimal contents of copper, iron (II), zinc and other impurities from the silica gel, and the filtered solution is then sent to the bio-oxidization process. Finally the precipitated silica gel, washed with water in the same separating equipment, is sent to a drying stage in a solar drying pad for two days. Thus, a technical-grade silica-gel is obtained as commercial byproduct of this process. Table 4 shows the chemical characterization of this silica gel. The iron content of 4.4% that gives this solid a yellow tint can be extracted by appropriate chemical methods for subsequent applications. The silica-free ferrous solutions (7) are then sent to the bioreactor for the production of ferric sulfate.

TABLE 4

Chemical Characterization of Silica Gel by product

|  |  | Cu | Fe | Si | Al |
|---|---|---|---|---|---|
| Initial ferrous slag leaching solution | g/L | 1.21 | 28.5 | 4.48 | 2.72 |
| Ferrous solution produced in the thermal treatment stage (80 a 95° C.) (1) | g/L | 1.11 | 26.8 | 0.11 | 2.49 |
| Ferrous solution produced in solid washing stage (2) | g/L | 0.81 | 20 | 0 | 1.74 |
| Final ferrous solution for bio-oxidization (1 + 2) | g/L | 1.04 | 25.1 | 0.08 | 2.3 |
| Final Silica gel residue (10% humidity) | % | 0.38% | 4.37% | 25.21% | 1.04% |

Example 3

This example describes the complete procedure of the pilot-scale bio-production of ferric sulfate from the leaching of granulated classified slag operated in fixed bed modules (equivalent to operation in dynamic heaps). FIG. 1 shows a flow diagram of the pilot plant used, that validates this invention and is described in this example. Following is a description of each operational area of the pilot-plant.

(1) Area for classification of granulated slag: The granulated slag (a), generated in slag-cleaning electric furnaces of Copper Smelting Plants, is transported to the slag classification area (2) This slag has a high moisture content as a result of the granulating process. It is deposited in solar drying pads on a polyethylene plastic covering or alternatively dried in a rotary kiln in order to reduce its water content to a residual moisture in the range of 0.1 to 0.05%. The dried slag is loaded into a receiving hopper and discharged onto a conveyor belt feeding a vibrating sift which separates into two particle-size fractions: oversize or coarse slag with particle-size over 1 mm diameter, and an under-sized slag or fine slag with particle-size under 0.1 cm. diameter. The latter is eliminated from the process and returned to the slag dump, whereas the coarse slag with particles of over 0.1 cm (3) diameter is transferred via conveyor belt to a coarse-slag storage area adjacent to the slag leaching area. The operation, which was carried out in a pilot plant, corresponded to a treatment of 640 kg/hr of fayalite slag issuing from a slag cleaning electric furnace, with 7% humidity, and deposited in a solar drying area or pad with a slag layer of 2 cm. The residence time of the slag in this area ranged between 3 and 5 hrs, under the following weather conditions in the location: 25° C. from 10 am to 5 pm in summer. The residual moisture of dry slag was 0.2%. Under these moisture conditions of the slag it was possible to carry out its classification with a vibrating sift, separating 354 kg/hr of coarse slag, from 0.1 to 0.5 cm in size to be used in slag leaching, and 286 kg/hr of a fine slag under 0.1 cm, which is returned to the slag dump.

The physical and chemical characterization of granulated classified slag with 0.2% moisture used in this invention is presented in Table 5.

TABLE 5

Chemical and physical characterization of granulated classified slag > 1 mm

| | Fe | Si | Al | Cu | Zn | Mo | As | Mg |
|---|---|---|---|---|---|---|---|---|
| Element | | | | | | | | |
| % | 45.2 | 13.2 | 1.84 | 1.15 | 2.54 | 0.22 | 0.18 | 0.1 |

Physical Properties

| | |
|---|---|
| Particle size, lower cutoff >0.1 cm.: P80 | 0.158 cm. |
| Bulk density | 2.0 Ton/m$^3$ |
| Humidity | 0.1 to 0.05% |

(2) Leaching of granulated classified slag in fixed-bed modules: Granulated classified slag (3) is arranged in a heap 1.8 m high with a crown 2 m long×2 m wide. The pilot heap is equipped at its base with a geo-membrane. This heap of previously granulated slag classified at particle size 100% larger than 0.1 cm (P80=0.158 cm.) and weighing 14.4 tons, is irrigated by installing on its crown a network of sprinklers placed every 20 cm, and connected to the leaching solution feed manifold containing 60-70 g/L of sulfuric acid, then irrigated at a flow rate of 20 L·hr$^{-1}$·m$^{-2}$. The irrigation solution used in this example comes from a typical industrial effluent (4) generated in copper hydrometallurgy process in addition to the added sulfuric acid (5). Table 6 shows the chemical composition of the actual irrigation solution applied in the irrigation of the granulated classified slag heap.

TABLE 6

Chemical Characterization of the Industrial Irrigation Solution

| | Al | Cu | Fe$^{3+}$ | Cl | Mg | Mn | Zn | Na | H$_2$SO$_4$ |
|---|---|---|---|---|---|---|---|---|---|
| Element | | | | | | | | | |
| g/L | 1.34 | 0.78 | 0.63 | 0.3 | 1.1 | 0.57 | 0.42 | 0.38 | 63.62 |

This solution comes from a stirred tank that conditions this irrigation solution to the previously mentioned acidity. The leaching solution (9) that drains from the leach heap is sent to a final accumulation pond for ferrous leach solution. The operation described includes 60 days of irrigation or a number of days defined by the requirements of the leached iron, a decision made on the basis of the leaching kinetics curve obtained in this pilot stage (FIG. 4). Ferrous solutions from heap drainage (9) are accumulated in a reception pool or pond and sent from this point to the area of purification of this solution.

Once the "depleted" slag heap has been drained, these slags are washed with water (6) at a rate of 20-100 L·hr$^{-1}$·m$^{-2}$ until an acid content in the solution in terms of pH in the range of 4-6 is achieved; this operation is extended 3-4 days from the residual slag washing. Wash water collected from depleted-slag modules is collected in an intermediate pond and partly recirculated to the slag-heap irrigation-solution conditioning-tank, whereas the leached and rinsed and drained depleted slag (8) are then transported to the slag dump as non-hazardous and environmentally stable waste according to leachability tests and other tests required by legislation.

The final ferrous solution, drained from slag heaps or modules and stored in a reception pond, has an average chemical and physical characterization seen in tables 7 and 8.

TABLE 7

Chemical Characterization of the Percolated Slag-Heap Solution

| Al g/L | Ca g/L | Cu g/L | Fe g/L | K g/L | Mg g/L | Mn g/L |
|---|---|---|---|---|---|---|
| 1.48 | 0.8 | 1.95 | 28.36 | 0.35 | 8.83 | 4.08 |

| Na g/L | Si g/L | Zn g/L | Cl g/L | As ppm | Mo ppm | Pb ppm |
|---|---|---|---|---|---|---|
| 2.93 | 3.74 | 2.6 | 0.38 | 40 | 59 | >20 |

TABLE 8

Physical properties of the percolated slag heaps

| | | |
|---|---|---|
| Viscosity | cP | 2.07 |
| Surface tension | dyn/cm | 68.7 |
| Density | g/cm$^3$ | 1.17 |
| Suspended solids | ppm | 22 |

(3) Abatement of silicon and other impurities in the slag leach solution by precipitation with lime slurry: FIG. 1 shows a flow chart of the pilot plant, which has a stirred tank for the preparation of lime slurry at 10% p/v transferred by gravity to stirred reactors for precipitation of impurities, arranged in series, (10 and 13). The slag leach solution stored in a reception pond is pumped to the first stirred reactor (10) for abatement of aluminum, silica and other impurities. Feed flows of slag leaching solution and lime slurry in the reactor (10) must be such that slurry with a pH ranging between 3.6 to 4.0 and residence time of 1 hour is achieved. To this end, the flowmeter is linked to the pH meter via a programmable logic controller (PLC). The second stirred reactor for aluminum abatement (13) is fed by overflow (12) from the reactor (10). In addition, lime slurry is also fed by gravity to the reactor from the lime slurry tank (13), forming a new slurry with a pH of 4.3 and residence time of 1 hour. The slurry going out (15) of the reactor (13) is received in an aeration tank from where it is sent to the filter press (17). The feeding pump sends the slurry from the aerator to the filter press. The treated and filtered ferrous solution (19) is sent to a storage tank for transportation to the bio-oxidization area. Tables 9 and 10 present the average chemical and physical characterization of the treated and filtered ferrous solution (19).

TABLE 9

Chemical Characterization of the Filtered Solution (after Silicon Abatement)

| Cu g/L | Fe g/L | Al g/L | Cl g/L | Si g/L | $H_2SO_4$ g/L | pH |
|---|---|---|---|---|---|---|
| 1.80 | 26.30 | 0.93 | 0.36 | 0.80 | 2.00 | 1.80 |

TABLE 10

Physical properties of the Filtered solution (after Silicon abatement)

| Viscosity | cP | 1.50 |
|---|---|---|
| Surface tension | dyn/cm | 69 |
| Density | g/cm$^3$ | 1.13 |
| Suspended solids | ppm | 7 |

The filtered solid (18), (metal hydroxides and gypsum) is stored and sent to a landfill. Table 11 presents the average chemical characterization of the solid solution obtained during silica precipitation. Also, Table 12 shows the results of the Toxicity Characteristic Leaching Procedure test (TCLP) applied to the filtered solid.

TABLE 11

Chemical Characterization of the Filtered Solid (Produced during Silicon abatement.)

| Cu % | Fe % | Al % | Cl % | Si % |
|---|---|---|---|---|
| 0.17 | 2.69 | 0.92 | 0.01 | 4.14 |

TABLE 12

Results of TCLP Test of the Filtered Solid (Produced during Silicon abatement.)

| | Lead mg/L | Cadmium mg/L | Mercury mg/L | Chromium mg/L | Barium mg/L | Selenium mg/L | Arsenic mg/L | Silver mg/L |
|---|---|---|---|---|---|---|---|---|
| Filtered Solid | <0.2 | 0.73 | <0.01 | <0.1 | <5.0 | <0.05 | <0.2 | <0.2 |
| Maximum Allowed | 5.00 | 1.00 | 0.20 | 5.00 | 100.00 | 1.00 | 5.00 | 5.00 |

(4) Bio-oxidization of ferrous solution:

The ferrous solution (19) obtained in the previous stage was oxidized in a bio-oxidization reactor (20) with a total volume of 256 L, with a reaction volume of 131 L and phase separator volume of 125 L.

To start the culture, 20 L of inoculum carrying microorganisms (22) of the genus *Leptospirillum* was mixed with 230 L of culture medium (23), with a composition as follows: 125 g $FeSO_4$/L, 0.25 g $(NH_4)_2SO_4$/L, 0.032 g $NaH_2PO_4.H_2O$/L, 0.013 g $KH_2PO_4$/L, 0.025 g $MgSO_4.7H_2O$/L, 0.005 g/L $CaCl_2$/L. The pH of the culture medium was adjusted to 1.4. The biomass support content was 40 g/L, consisting mainly of iron precipitates and to a lesser degree, of diatomaceous earth. To allow the growth of microorganisms in the bioreactor, air was supplied (26) with a flow-volume of 84 L/min. The reactor temperature was controlled at 32° C. through the provision of heat (28). The bioreactor pH was set at a value of 1.4 by addition of $H_2SO_4$, (25).

The bioreactor was operated in continuous mode for 19 hours, fed with culture medium of the indicated composition, at pH 1.2, with a flow-volume of 30 L/h. The hydraulic residence time of the solution in the reaction zone was 5.2 h. The bioreactor was equipped with temperature sensors, dissolved oxygen, redox potential and pH.

During continuous operation, 419 L of the ferrous solution were fed, with a composition as shown in Table 9, to which the following nutrients were added: 0.25 g $(NH_4)_2SO_4$/L, 0.032 g $NaH_2PO_4.H_2O$/L, 0.013 g $KH_2PO_4$/L, 0.025 g $MgSO_4.7H_2O$/L, 0.005 g/L $CaCl_2$/L. The pH of the culture medium was adjusted to 1.2.

Table 13 indicates key operational data and results of this phase.

TABLE 13

Operational conditions and global results of the ferrous solution oxidization stage in a bioreactor.

| Operation Time [hours] | 16 |
|---|---|
| Average power flow-volume [L/h] | 29.96 |
| Solution input volume [L] | 419 |
| Feeding solution pH | 1.18 |
| Effluent solution pH | 1.52 |
| Feeding viscosity [cP] | 1.74 |
| Effluent viscosity [cP] | 1.76 |
| Iron productivity (III) [Kg h$^{-1}$ m$^{-3}$] | 4.2 |
| Acid input volume [L] | 1.1 |
| Acid consumption [L/Kg Fe(III) generated] | 0.141 |
| Produced bacteria [cells] | $6.21 \cdot 10^{13}$ |
| Biomass productivity [h$^{-1}$ m$^{-3}$ cells] | $3.05 \cdot 10^{10}$ |

The invention claimed is:

1. A hydrometallurgical procedure for producing ferric sulfate solutions comprising an iron concentration greater than 20 g/L, and less than 1 g/L of silicon and other impurities, wherein the process is carried out in continuous mode in three sequential steps comprising:

1) acid leaching fayalite slag in a leaching heap, wherein the fayalite slag comprises fayalite slag from an electric furnace for reductive slag cleaning and is granulated and classified 100% with a particle diameter greater than 0.1 cm.;

2) collecting percolated leaching liquid from the leaching heap and removing silicon, aluminum and other impurities in the percolated leaching liquid, through thermal coagulation and precipitation of colloidal silica, or alternatively, neutralization with lime slurry, to form a ferrous solution comprising less than 1 g/L of silicon; and 3) bio-oxidizing the ferrous solution in a bioreactor to form the ferric sulfate solution comprising an iron concentration greater than 20 g/L.

2. The hydrometallurgical procedure according to claim 1, wherein the fayalite slag is dried prior to acid leaching.

3. The hydrometallurgical procedure according to claim 1, wherein the leaching heap is 0.70 m to 3 m high and is constructed with appropriate mechanical and hydraulic stability properties, in which efficient percolation or drainage of the heap or a fixed bed comprising the heap is maintained for an extended operating time of up to 100 days.

4. The hydrometallurgical procedure according to claim 1, wherein the leaching heap is operated in dynamic mode in which the leaching heap is irrigated with solutions of sulfuric acid in concentrations of 40-60 g/L at an irrigation rate of 20-70 L/hm$^2$ and a leaching cycle of 40-100 days.

5. The hydrometallurgical procedure according to claim 1, comprising purifying the collected leaching liquid by controlled precipitation of colloidal silica contained in the leaching liquid by thermal coagulation and flocculation to separate the colloidal silica obtained from the leaching liquid and subsequently washing the separated colloidal silica to obtain a byproduct of silica gel, $SiO_2.2H_2O$.

6. The hydrometallurgical procedure according to claim 1, wherein colloidal silica and other impurities are precipitated from the collected leaching liquid by neutralizing the leaching liquid by adding a lime slurry in a stirred reactor, at room temperature and with pH control, into provide:

(a) a ferrous solution comprising less than 1 g/L of silicon, and (b) a final residue of precipitated silica and other impurities within a matrix of gypsum and ferric hydroxide.

7. The hydrometallurgical procedure according to claim 1, wherein the bioreactor is an "air-lift" bioreactor which operates at a temperature of 20-40° C., air-injected with a biomass immobilized in an inert material, and iron-oxidizing microorganisms adapted to this process, thereby producing a final solution of ferric sulfate, with a ferric-ion concentration above 50 g/L, with low impurity content (<1 g/L) and productivity over 4.2 Kg Ferric $h^{-1}$ $m^{-3}$.

8. The hydrometallurgical procedure according to claim 7, wherein the microorganisms comprise acidophilic microorganisms capable of oxidizing ferrous iron.

9. The hydrometallurgical process according to claim 8, wherein the bioreactor comprises iron-oxidizing microorganisms belonging to the genus *Acidimicrobium, Acidithiobacillus, Ferrimicrobium, Ferroplasma, Leptospirillum, Sulfobacillus*, or *Thiobacillus*.

10. The hydrometallurgical process according to claim 7, wherein iron-oxidizing microorganism comprises *Acidimicrobium ferrooxidans, Acidithiobacillus ferrooxidans, Ferrimicrobium acidiphilum, Ferroplasma acidiphilium, Leptospirillum ferrooxidans, Leptospirillum ferriphilum, Sulfobacillus* spp., or *Thiobacillus prosperus*.

* * * * *